(12) United States Patent
Kim et al.

(10) Patent No.: US 9,885,719 B2
(45) Date of Patent: Feb. 6, 2018

(54) COMPOSITION COMPRISING LYSOPHOSPHATIDYLCHOLINE AND HOMOCYSTEIC ACID FOR OVARIAN CANCER DIAGNOSIS AND METHOD USING THE SAME

(71) Applicant: Ewha University-Industry Collaboration Foundation, Seoul (KR)

(72) Inventors: Seung Cheol Kim, Seoul (KR); Byong Chul Yoo, Gyeonggi-do (KR); Kyung-Hee Kim, Seoul (KR); Yun Hwan Kim, Gyeonggi-do (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 14/398,438

(22) PCT Filed: Aug. 21, 2014

(86) PCT No.: PCT/KR2014/007760
§ 371 (c)(1),
(2) Date: Oct. 31, 2014

(87) PCT Pub. No.: WO2015/026171
PCT Pub. Date: Feb. 26, 2015

(65) Prior Publication Data
US 2016/0266128 A1    Sep. 15, 2016

(30) Foreign Application Priority Data
Aug. 21, 2013 (KR) .................. 10-2013-0098855

(51) Int. Cl.
*G01N 33/92* (2006.01)
*G01N 33/574* (2006.01)
*G01N 33/68* (2006.01)

(52) U.S. Cl.
CPC ... *G01N 33/57449* (2013.01); *G01N 33/6815* (2013.01); *G01N 33/92* (2013.01); *G01N 2405/04* (2013.01)

(58) Field of Classification Search
CPC ......... G01N 33/57449; G01N 33/6815; G01N 33/92; G01N 2405/04; Y10S 436/808
See application file for complete search history.

(56) References Cited

U.S. PATENT DOCUMENTS

| | | | |
|---|---|---|---|
| 8,871,438 B2 | 10/2014 | Lee et al. | 250/287 |
| 2002/0123084 A1 | 9/2002 | Mills et al. | 435/7.23 |
| 2013/0065266 A1 | 3/2013 | Lee et al. | 250/287 |
| 2013/0206977 A1 | 8/2013 | Yoo et al. | 702/23 |
| 2013/0231869 A1 | 9/2013 | Yoo et al. | 702/19 |

FOREIGN PATENT DOCUMENTS

KR    10-0487911    9/2004

OTHER PUBLICATIONS

Van Der Vekiens et al., Human and equine cardiovascular endocrinology: beware to compare, Cardiovascular Endocrinology 2013, vol. 2, No. 4, pp. 67-76.*
Torzewski et al., Animal Models of C-Reactive Protein, Hindawl Publishing Corporation, Mediators of Inflammation, vol. 2014, Article ID 683598, 2014, pp. 1-7.*
Letter/Written Disclosure of the Supplemental Information Disclosure Statement for the above-referenced application, filed herewith on May 5, 2017, 2 pages.
Written Opinion, dated Dec. 1, 2014, in connection with corresponding International Patent Application No. PCT/KR2014/007760 [English translation], 4 pages.
International Preliminary Report on Patentability, dated Feb. 23, 2016, in connection with corresponding International Patent Application No. PCT/KR2014/007760, 5 pages.
Letter/Written Disclosure of the Information Disclosure Statement for the above-referenced application, mailed on May 26, 2015, 2 pages.
Bligh, E. and W. Dyer, "A rapid method of total lipid extraction and purification," Can J Biochem Physiol. 37(8):911-917 (1959).
English language abstract of Korean Patent No. KR 10-0487911, published Apr. 27, 2005 (Korean Patent Pub. No. KR 10-2004-0062819; Korean Patent App. No. KR 10-2003-0000350), World Intellectual Property Office, [Accessed on Apr. 13, 2015] 1 page.
Kim et al., "Differential levels of L-homocysteic acid and lysophosphatidylcholine (16:0) in sera of patients with ovarian cancer." Oncol Lett. 8(2):566-574 (2014).
Lukyanova, N., "Characteristics of homocysteine-induced multidrug resistance of human MCF-7 breast cancer cells and human A2780 ovarian cancer cells", Experimental Oncology, 32(1):10-14 (2010).
Machine translation of Korean Patent No. KR 10-0487911, published Apr. 27, 2005 (Korean Patent Pub. No. KR 10-2004-0062819; Korean Patent App. No. KR 10-2003-0000350), Korean Intellectual Property Office, [Accessed on Apr. 13, 2015] 9 pages.
Schulz, R., "Homocysteine as a biomarker for cognitive dysfunction in the elderly", Current Opinion in Clinical Nutrition & Metabolic Care, 10:718-723 (2007).
Sutphen et al., "Lysophospholipids are potential biomarkers of ovarian cancer", Cancer Epidemiology, Biomarkers & Prevention, 13(7):1185-1191 (2004).
International Search Report, dated Dec. 1, 2014, in connection with corresponding International Application No. PCT/KR2014/007760 [English translation] 3 pages.

* cited by examiner

*Primary Examiner* — Gary Counts
(74) *Attorney, Agent, or Firm* — Dentons US LLP; Stephanie Seidman

(57) ABSTRACT

Provided are methods of treating a subject for of ovarian cancer, the method including using lysophosphatidylcholine (16:0) and homocysteic acid, which are low-mass ions present in biological samples, to diagnose whether treatment should be provided. The method enables ovarian cancer to be diagnosed in a cost-effective, rapid and accurate manner.

7 Claims, 19 Drawing Sheets

| Sample No. | 183.96 m/z | 478.33 m/z | Sample No. | 183.96 m/z | 478.33 m/z |
|---|---|---|---|---|---|
| C1 | 177013 | 376781 | OVC1 | 14153 | 30741 |
| C2 | 69756 | 137502 | OVC2 | 5859 | 13745 |
| C3 | 124532 | 272566 | OVC3 | 7971 | 15462 |
| C5 | 25420 | 66997 | OVC4 | 8396 | 19590 |
| C6 | 54801 | 128622 | OVC5 | 20228 | 53475 |
| C7 | 37451 | 84449 | OVC6 | 16271 | 39552 |
| C8 | 83913 | 172936 | OVC7 | 32559 | 69217 |
| C9 | 24680 | 64998 | OVC8 | 25213 | 60890 |
| C10 | 24203 | 53327 | OVC9 | 12003 | 30286 |
| C11 | 154157 | 376840 | OVC10 | 26121 | 59037 |
| C12 | 22627 | 51433 | OVC11 | 33905 | 51453 |
| C13 | 48125 | 102808 | OVC12 | 51453 | 115718 |
| C14 | 52038 | 109721 | OVC13 | 40846 | 87236 |
| C15 | 45143 | 104486 | OVC14 | 68258 | 149730 |
| C16 | 10764 | 24637 | OVC15 | 49476 | 114076 |
| C17 | 4301 | 10910 | OVC16 | 53280 | 132663 |
| C18 | 6538 | 15969 | OVC17 | 49151 | 109521 |
| C19 | 5664 | 8595 | OVC18 | 40636 | 84156 |
| C20 | 1894 | 3979 | OVC19 | 35516 | 78462 |
| | | | OVC20 | 59064 | 130141 |
| | | | OVC21 | 38533 | 80979 |
| | | | OVC22 | 14389 | 31269 |
| | | | OVC23 | 7779 | 15915 |
| | | | OVC24 | 35065 | 83313 |
| | | | OVC25 | 12879 | 29815 |

Stratified screening of OVC using HCA and LPC (16:0)

ically, Korea in the year 2002, about 1,000-1,200 new ovarian cancer patients are diagnosed each year, and ovarian cancer is a gynecologic cancer that is the second most common after cervical cancer. Epithelial ovarian cancer accounting for about 90% of ovarian cancer is diagnosed after stage III of development in most cases, and thus patients with epithelial ovarian cancer have a very low 5-year survival rate of 40% or less.

COMPOSITION COMPRISING LYSOPHOSPHATIDYLCHOLINE AND HOMOCYSTEIC ACID FOR OVARIAN CANCER DIAGNOSIS AND METHOD USING THE SAME

RELATED APPLICATIONS

This application is the U.S. National Stage of International Application. No. PCT/KR2014/007760, filed 21 Aug. 2014, which claims benefit of priority to Korean Patent Application No. KR 10-2013-0098855, filed 21 Aug. 2013, which is incorporated by reference herein.

BACKGROUND OF THE INVENTION

Field of the Invention

The present invention relates to diagnosis of ovarian cancer using lysophosphatidylcholine (16:0) and homocysteic acid, which are low-mass ions present in biological samples.

Description of the Prior Art

Ovarian cancer is a malignant tumor occurring in the ovaries and is most often found in women aged 50-70 years. According to cancer statistics in Korea in the year 2002, about 1,000-1,200 new ovarian cancer patients are diagnosed each year, and ovarian cancer is a gynecologic cancer that is the second most common after cervical cancer. Epithelial ovarian cancer accounting for about 90% of ovarian cancer is diagnosed after stage III of development in most cases, and thus patients with epithelial ovarian cancer have a very low 5-year survival rate of 40% or less.

Patients with ovarian cancer show slight symptoms, and about 60% of the patients visit hospitals after the cancer developed significantly. For this reason, it is recommended that women to be regularly examined for ovarian cancer about once a year, even if there are no symptoms of ovarian cancer. Methods that are currently used to diagnose ovarian cancer include the review of medical history and family history, the palpation of ovary, ultrasound examination, and a blood testing method for measuring whether the expression of CA125 biomarker increased. If a patient is suspected of having ovarian cancer, the cancer is identified by CT or MRI. However, these methods have disadvantages in that they can diagnose ovarian cancer only after the cancer developed significantly, may provide inaccurate diagnosis, and cause discomfort to patients during diagnosis.

Meanwhile, the spectra of ions in blood can be extracted using a MALDI-TOF spectrometer. Mass spectrometry used in conventional proteomic analysis was performed to analyze substances mainly in the mass range of 800-2500 m/z, because this range is the mass range of peptides cleaved from proteins by trypsin. In addition, the use of a MALDI-TOF mass spectrometer can also extract the mass spectra of low-mass ions. However, because the low-mass range of about 800 m/z or less is a range in which the peaks of a matrix that is an object to be analyzed coexist, studies on this range have not been actively conducted.

Mass spectra extracted using a MALDI-TOF mass spectrometer can be imported into MarkerView™ software and subjected to principal component analysis-based linear discriminant analysis (PCA-DA) using MarkerView™ software in order to diagnose ovarian cancer.

SUMMARY OF THE INVENTION

It is an object of the present invention to provide a composition for diagnosing ovarian cancer, the composition comprising lysophosphatidylcholine (16:0) and L-homocysteic acid, which are low-mass ions.

Another object of the present invention is to provide a method of providing information for diagnosis of ovarian cancer by detecting lysophosphatidylcholine (16:0) and L-homocysteic acid in a biological sample collected from a subject.

Still another object of the present invention is to provide a kit for diagnosing ovarian cancer using lysophosphatidylcholine (16:0) and L-homocysteic acid.

Still another object of the present invention is to provide a method for screening an ovarian cancer-treating agent by measuring whether the concentrations of lysophosphatidylcholine (16:0) and L-homocysteic acid are changed.

To achieve the above objects, the present inventors have selected two peaks, which consistently show a significant difference from those of non-ovarian cancer patients, from the mass spectra of biological samples obtained from ovarian cancer patients, and have found that the selected peaks are the peaks of lysophosphatidylcholine (16:0) and L-homocysteic acid, which are low-mass ions, thereby completing the present invention.

Accordingly, the present invention provides a composition for diagnosing ovarian cancer, which comprises lysophosphatidylcholine (16:0) and L-homocysteic acid.

As used herein, the term "lysophosphatidylcholine (16:0)" refers to a lysophosphatidylcholine, a kind of lysophospholipid, which is composed of 16 carbon atoms linked by only single bonds without a double bond.

L-homocysteic acid is a natural amino acid, and it is known that the concentration of L-homocysteic acid increases in dementia and cardiac diseases.

The present inventors have found that the use of lysophosphatidylcholine (16:0) together with L-homocysteic acid in diagnosis shows an excellent effect on the diagnosis of ovarian cancer, thereby completing the present invention. For example, the use of a method schematically shown in FIG. 11 of this application showed a diagnostic sensitivity of 88.0% and a diagnostic specificity of 73.68%.

The present invention also provides a method for providing information for diagnosis of ovarian cancer, the method comprising the steps of: 1) measuring the concentration of L-homocysteic acid in a biological sample collected from a subject; and 2) measuring the concentration of lysophosphatidylcholine (16:0) in the biological sample collected from the subject.

The concentration of lysophosphatidylcholine (16:0) or L-homocysteic acid can vary depending on measurement conditions, measurement kits or devices, and the amounts of samples. Thus, whether a subject is an ovarian cancer patient can be diagnosed by comparing the concentration of lysophosphatidylcholine (16:0) or L-homocysteic acid in a biological sample of the subject with that in a biological sample of a non-ovarian cancer patient as a negative control and/or a biological sample of an ovarian cancer as a positive control under the same conditions. Alternatively, standard numerical data obtained from non-ovarian cancer patients and ovarian cancer patients under standard conditions may also be used to diagnose whether a subject has ovarian cancer.

Step 1) or step 2) in the method may comprise the steps of: A) acquiring the mass spectrum of the biological sample obtained from the subject; and B) comparing the acquired mass spectrum with the mass spectrum of a biological sample of a non-ovarian cancer patient or the mass spectrum of a biological sample of an ovarian cancer patient to determine the difference in the concentration of lysophosphatidylcholine (16:0) or L-homocysteic acid therebetween.

In the method, step 1) or step 2) may be performed using an antigen-antibody binding reaction.

In one embodiment of the present invention, step 1) may be performed by measuring whether the concentration of L-homocysteic acid detected in the biological sample obtained from the subject is higher than 10 nmol/ml. If the concentration of L-homocysteic acid detected is higher than 10 nmol/ml, the subject may be diagnosed as an ovarian cancer patient, and step 2) may not be performed. However, if the concentration of L-homocysteic acid detected is 10 nmol/ml or less, step 2) may be performed to compare the concentration of lysophosphatidylcholine (16:0) in the subject with that in the non-ovarian cancer patient or the ovarian cancer patient to determine whether the subject has ovarian cancer.

In another embodiment of the present invention, step 1) may be performed using ELISA (enzyme-linked immunosorbent assay), and step 2) may be performed using LC-MS/MS.

In still another embodiment of the present invention, step 1 in the method may be performed before step 2).

The biological sample may be selected from the group consisting of whole blood, serum, plasma, saliva, phlegm, peritoneal fluid, cyst fluid, and urine.

The present invention also provides a kit for diagnosing ovarian cancer, which comprises: an antibody that binds specifically to lysophosphatidylcholine (16:0) or a fragment thereof; and an antibody that binds specifically to L-homocysteic acid or a fragment thereof. In one embodiment of the present invention, the kit for diagnosing ovarian cancer may comprise: an antibody that binds specifically to a fragment of lysophosphatidylcholine (16:0); and an antibody that binds specifically to a fragment of L-homocysteic acid.

The present invention also provides a method for screening an agent for treating ovarian cancer, the method comprising the steps of: 1) administering a test substance to an animal model; and 2) measuring the concentrations of lysophosphatidylcholine (16:0) and L-homocysteic acid in a biological sample obtained from the animal model. The animal model may be an ovarian cancer animal model.

DETAILED DESCRIPTION OF THE INVENTION

Figure 1A:
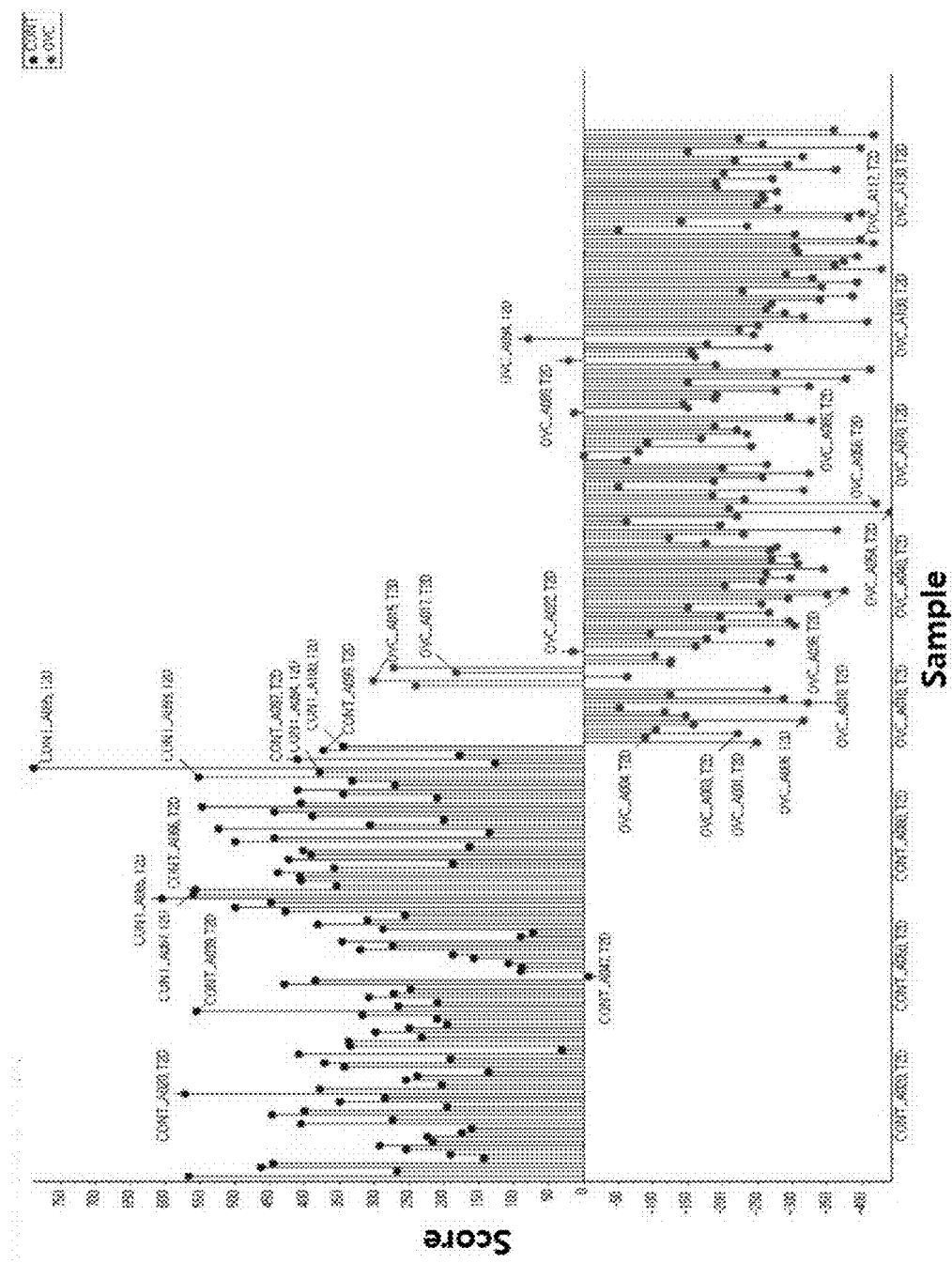
FIGS. 1a to 3b show discriminant scores obtained from ovarian cancer patients (negative numbers) and non-ovarian cancer patients (positive numbers) by importing the mass spectra of low-mass ions, extracted using a MALDI-TOF mass spectrometer, into MarkerView™, followed by PCA-DA. The experiment was repeated six times in total, and thus each graph in FIGS. 1a to 3b shows the results of each experiment, and each of FIGS. 1a to 3b shows two graphs (1a and 1b, 2a and 2b, 3a and 3b).

As used herein, the term "biological sample" is meant to include samples such as whole blood, serum, plasma, urine, feces, phlegm, saliva, tissue, cells, cell extracts, and in vitro cell cultures, but is not limited thereto. In examples as described below, the sera of patients or non-patients were used as biological samples.

As used herein, the term "intensity" refers to a value that is obtained by a MALDI-TOF mass spectrometer and is correlated with the concentration of a mass ion corresponding to a peak.

As used herein, the term "normalization" refers to matching data ranges or making distributions similar to each other. The normalization may be performed using mean values, median values, etc., but is not limited thereto, and in some cases, various known normalization methods may be applied. In an embodiment of the present invention, normalization may be performed by obtaining the subtotals of intensities for each sample, averaging the subtotals for each sample, and then multiplying each peak intensity by a multiplying factor so that the subtotal of intensities for each sample is consistent with the average of the subtotals. After such normalization, the subtotals of intensities for each sample become uniform.

As used herein, the term "Pareto scaling" refers to subtracting the mean value of mass values from each normalized peak intensity and dividing the subtracted value by square root of the standard deviation. While autoscaling, a more general scaling version, completely offsets data size information by dividing it by the standard deviation, the Pareto scaling has an advantage in that noise amplification can be avoided by partially maintaining data size information.

As used herein, the term "weighting factor" refers to a factor to adjust the numerical size of the data after multiplication by weight to a proportional relationship with the importance from the statistical viewpoint. One example of the weighting factor may be a factor loading which is obtained as a result of principle component analysis-based linear discriminant analysis (PCA-DA) in the Examples described below.

As used herein, the term "low-mass ion" refers to ions having a mass value of less than 1500 m/z, as acquired by a MALDI-TOF spectrometer or the like.

In the present invention, the mass value measured by a MALDI-TOF mass spectrometer includes the error range of "±0.1 m/z". This is because a certain error may be generated depending on the experimental environment. The error range may be "±0.5 m/z" depending on the experimental environment.

It should be noted that the mass value measured by the MALDI-TOF mass spectrometer in the present invention is the mass value acquired in a positive mode of the MALDI-TOF mass spectrometer.

In the present invention, the code of the weighting vector may be determined to be positive if the discriminant score is positive, while it is determined to be negative if the discriminant score is negative. The factor loading vector in the PCA mathematically corresponds to eigenvector whose code may be determined arbitrarily. That is, mathematically, the values are considered equal according to the eigenvalue problem, even when the computed factor loading the eigenvalue problem, even when the computed factor loadings per mass ions are multiplied by −1 and thus change code. However, the negative value of a discriminant score is considered to indicate positivity, while the positive value of the discriminant score is considered to indicate negativity. It should be noted that the code of the eigenvector is adjusted in the present invention so that the positive discriminant score indicates negativity and the negative discriminant score indicates positivity, but the scope of the invention is not limited thereto.

Hereinafter, the present invention will be described in further detail. It is to be understood, however, that these examples are for illustrative purposes only and are not intended to limit the scope of the present invention.

Reagents and solvents as mentioned below were purchased from Honeywell Burdick & Jackson®, unless specified otherwise.

Sample Preparation—Subjects from which Sera are to be Collected

Sera were collected from 142 ovarian cancer patients and 100 non-ovarian cancer patients. Information about the state of ovarian cancer in the ovarian cancer patients is described in Table 1 below.

TABLE 1

|  |  | Ovarian cancer (n = 142) | Control (n = 100) |
|---|---|---|---|
| Age, Mean ± SD |  | 52 ± 13 | 51 ± 13 |
| Stage, n (%) | IA | 37 (26.1) |  |
|  | IB | 2 (1.4) |  |
|  | IC | 12 (8.5) |  |
|  | IIA | 0 (0) |  |
|  | IIB | 1 (0.7) |  |
|  | IIIA | 0 (0) |  |
|  | IIIB | 1 (0.7) |  |
|  | IIIC | 77 (54.2) |  |
|  | IV | 12 (8.5) |  |
| Histology, n (%) | Serous | 90 (63.4) |  |
|  | Mucinous | 23 (16.2) |  |
|  | Endometrioid | 8 (5.6) |  |
|  | Clear cell | 11 (7.7) |  |
|  | Transitional cell | 7 (4.9) |  |
|  | Mixed | 3 (2.1) |  |
| Grade, n (%) | Mild | 24 (16.9) |  |
|  | Moderate | 35 (24.6) |  |
|  | Severe | 83 (58.5) |  |

For diagnosis and the determination of the stage and range of diseases, all the ovarian cancer patients underwent staging operations, including hysterectomy, adnexectomy, pelvic lymphadenectomy, para-aortic lymphadenectomy, omentectomy, and peritoneal cytology, and the diagnosis and stage of ovarian cancer were finally determined based on the results of pathological examination.

EXAMPLES

Example 1: Determination of Low-Mass Ion Peaks for Diagnosis of Ovarian Cancer 1-1: Serum Preparation and Mass Spectrum Measurement The Bligh and Dyer method (Bligh, E. G and Dyer, W. J (1959)—Canadian Journal of Biochemistry and Physiology, vol. 37, page 911) was applied to selectively extract fatty acids from sera while ruling out 80% or more of proteins.

A four-fold volume of methanol/chloroform (2:1, v/v) was incubated with 25 µl of serum for 10 min at room temperature after vigorous vortexing. The mixture was centrifuged at 6,000×g for 10 min at 4° C. The supernatant obtained was completely dried in a concentrator for 1 hr, and dissolved in 30 L of 50% acetonitrile/0.1% trifluoroacetic acid (TFA) on a vortexer for 30 min. The solution was mixed (1:12, v/v) with an a-cyano-4-hydroxycinnamic acid solution (1:12, v/v), and 1 µl of the mixture was spotted on the MALDI-target for analysis. Individual mass spectra from serum extracts of patients were obtained using a 4700 Proteomics Analyzer (AB SCIEX, Poster City, Calif.). The mass-spectral data represent the average of 20 accumulated spectra. All individual peak areas were normalized to total area up to 2,500 m/z. To minimize experimental error, variable factors including focus mass, laser intensity, target plate, data acquisition time were tested. Ideal focus mass and laser intensity were fixed at 500 m/z and 5,000, respectively. With the fixed focus mass and laser intensity, one sample was analyzed 6 times in different extraction and data acquisition time in order to examine reproducibility.

Each graph in the figures shows the results of each measurement, and each of the figures shows two graphs.

1-2: Selection of Low-Mass Ions for Diagnosis of Ovarian Cancer

MALDI-TOP mass spectra, formatted as T2D files, were imported into MarkerView™ Software version 1.2 (Applied Biosystems/MDS Sciex, Toronto, Canada).

The import was performed under the conditions shown in Table 2 below.

TABLE 2

| Mass tolerance | 100 ppm |
|---|---|
| Minimum required response | 100 |
| Maximum number of peaks | 5000 |

MarkerView™ includes a number of normalization methods, and among these methods, "Normalization Using Total Area Sums" was used to perform normalization. According to this method, partial sums of the intensities of the respective samples were calculated and averaged, and then each peak intensity was multiplied by a scaling factor so that the sums of the respective samples were in agreement with the average values. As a result, the partial sums of the intensities of the respective samples became uniform after the normalization.

Next, the normalized peak intensities were Pareto-scaled. Specifically, the peak intensities were Pareto-scaled by subtracting the average values of the respective mass ions from the respective normalized peak intensities and dividing the same by the square root of the standard deviation.

Next, with respect to the Pareto-scaled peak intensities, discriminant scores (DS) were computed by performing the principal component analysis-based linear discriminant analysis (PCA-DA). Specifically, the PCA-DA was performed by two stages to obtain factor loadings, which are the weighting factors of the respective mass ions, and the Pareto-scaled intensities were multiplied by the factor loadings. As shown in Table 2 above, the maximum number of peaks was 5,000, and sufficient samples were also imported, and thus 5,000 factor loadings were computed. Thus, one DS was computed by summing 5,000 terms. The results were analyzed by t-test.

Figure 1B:
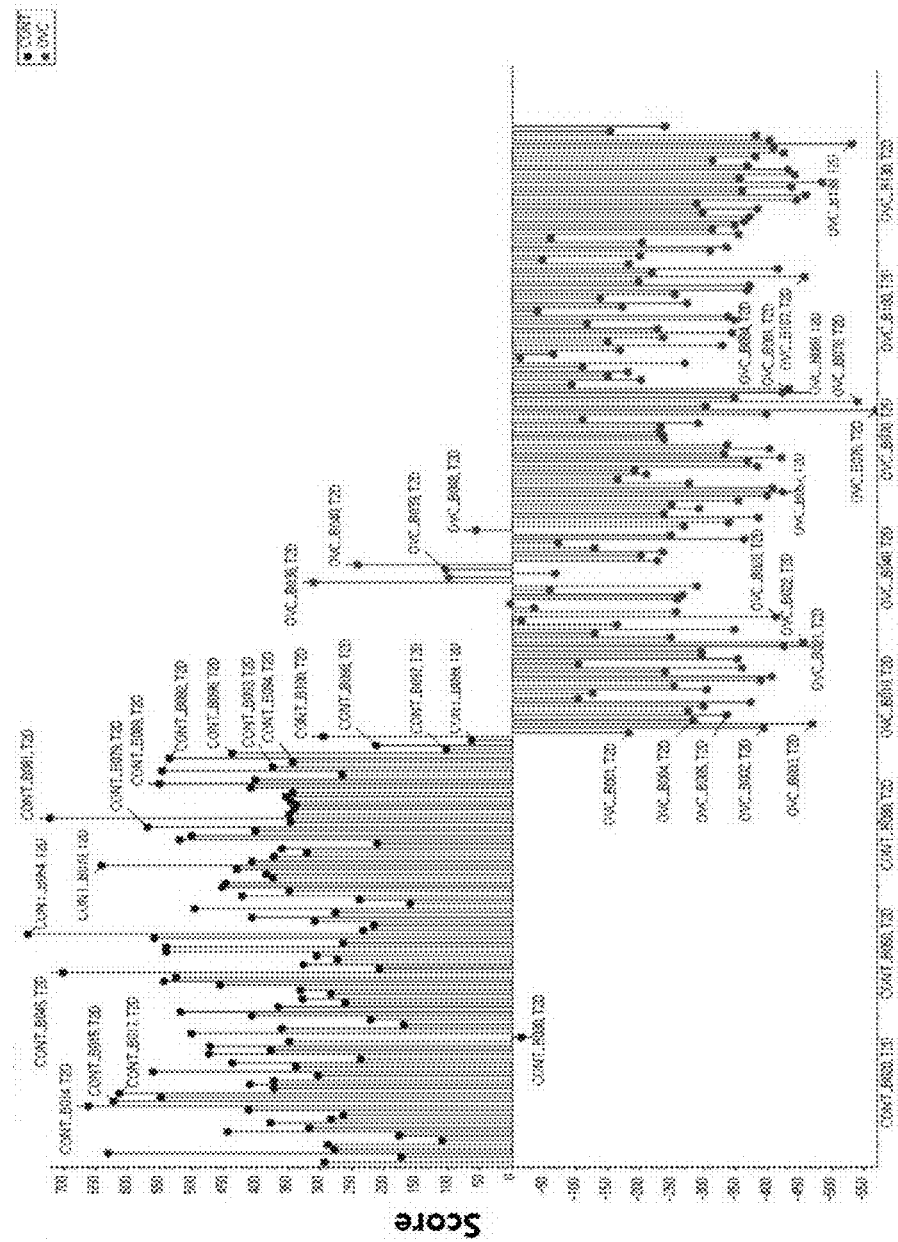
Figure 2A:
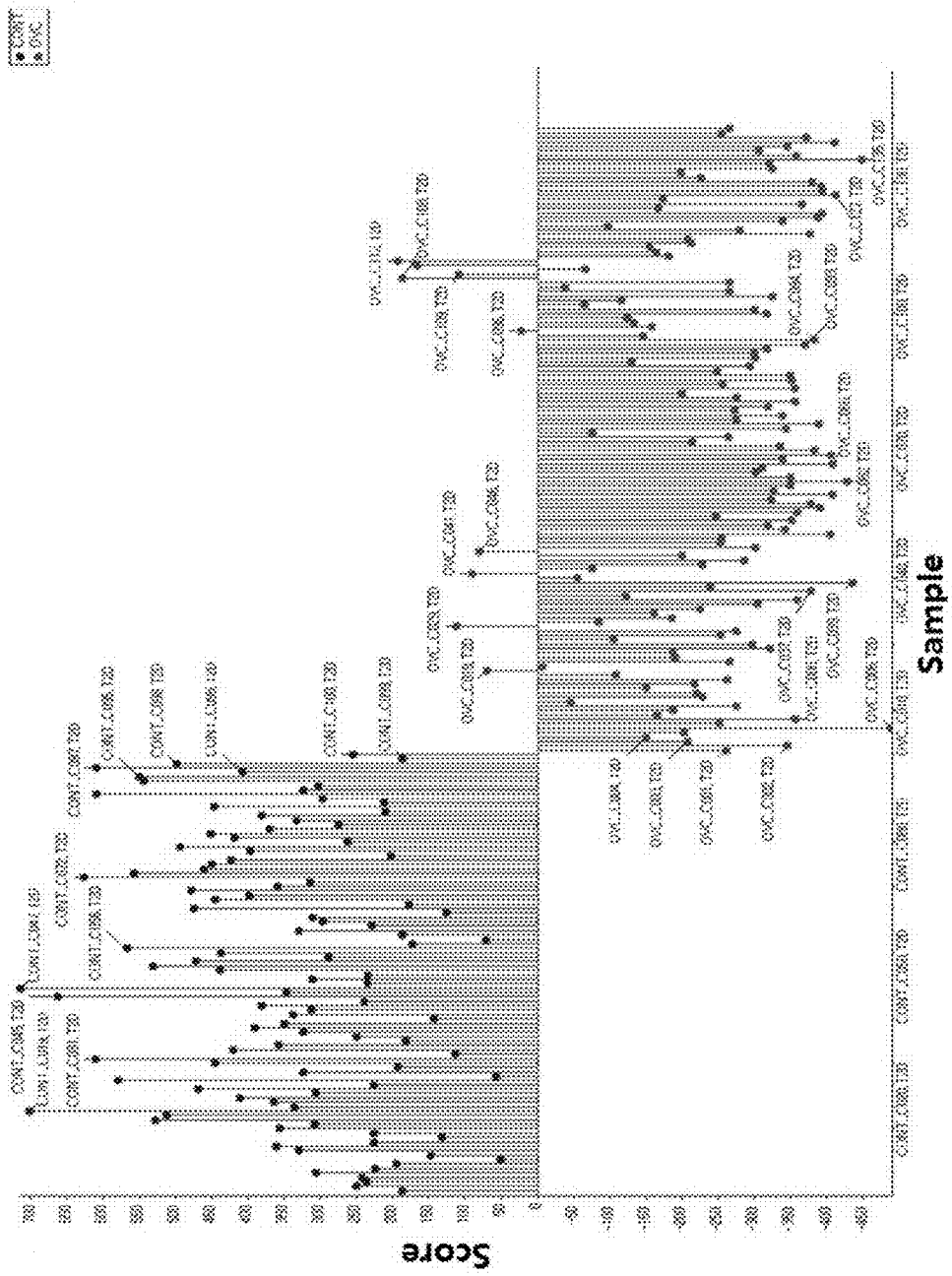
Figure 2B:
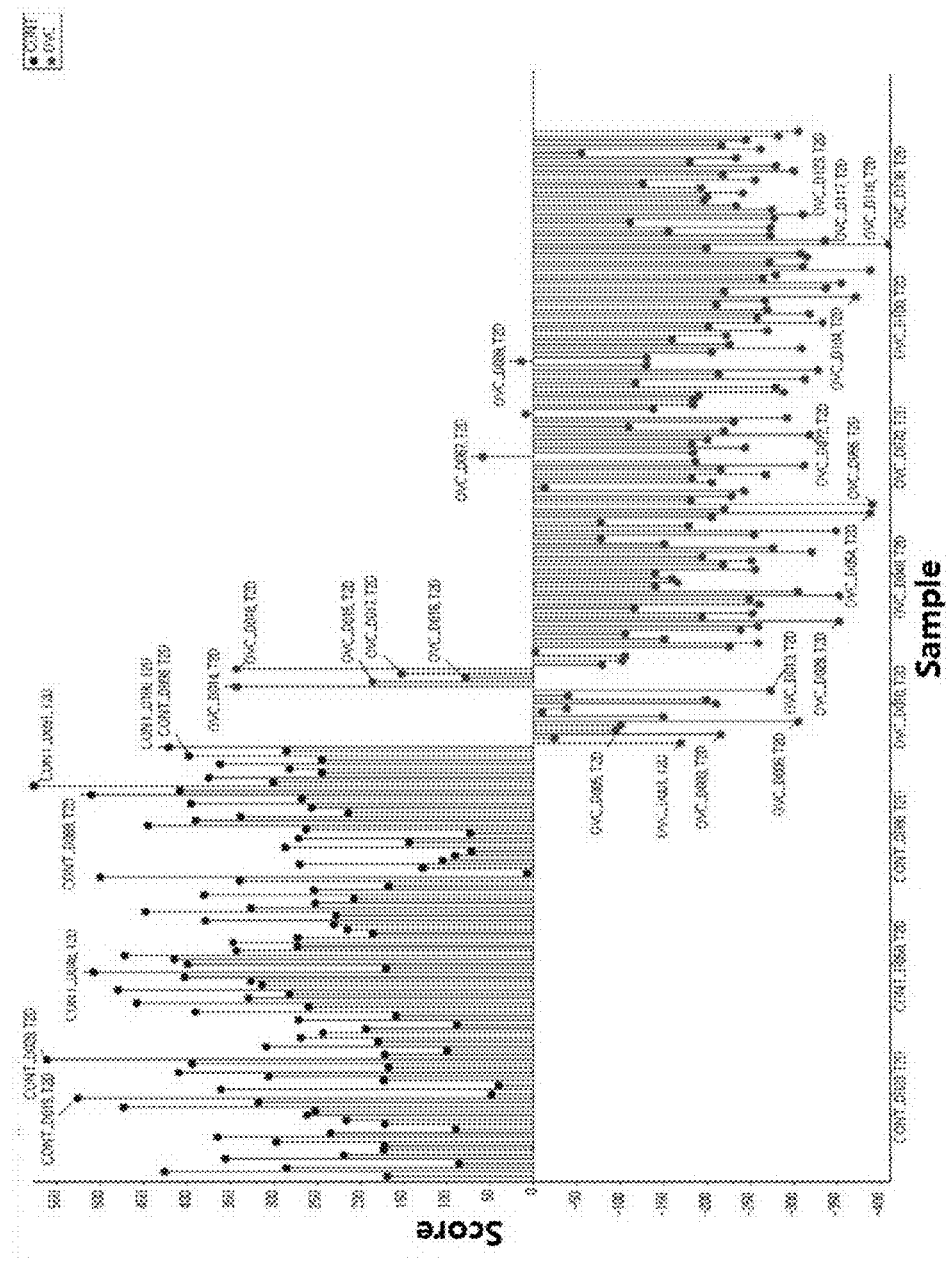
Figure 3A:
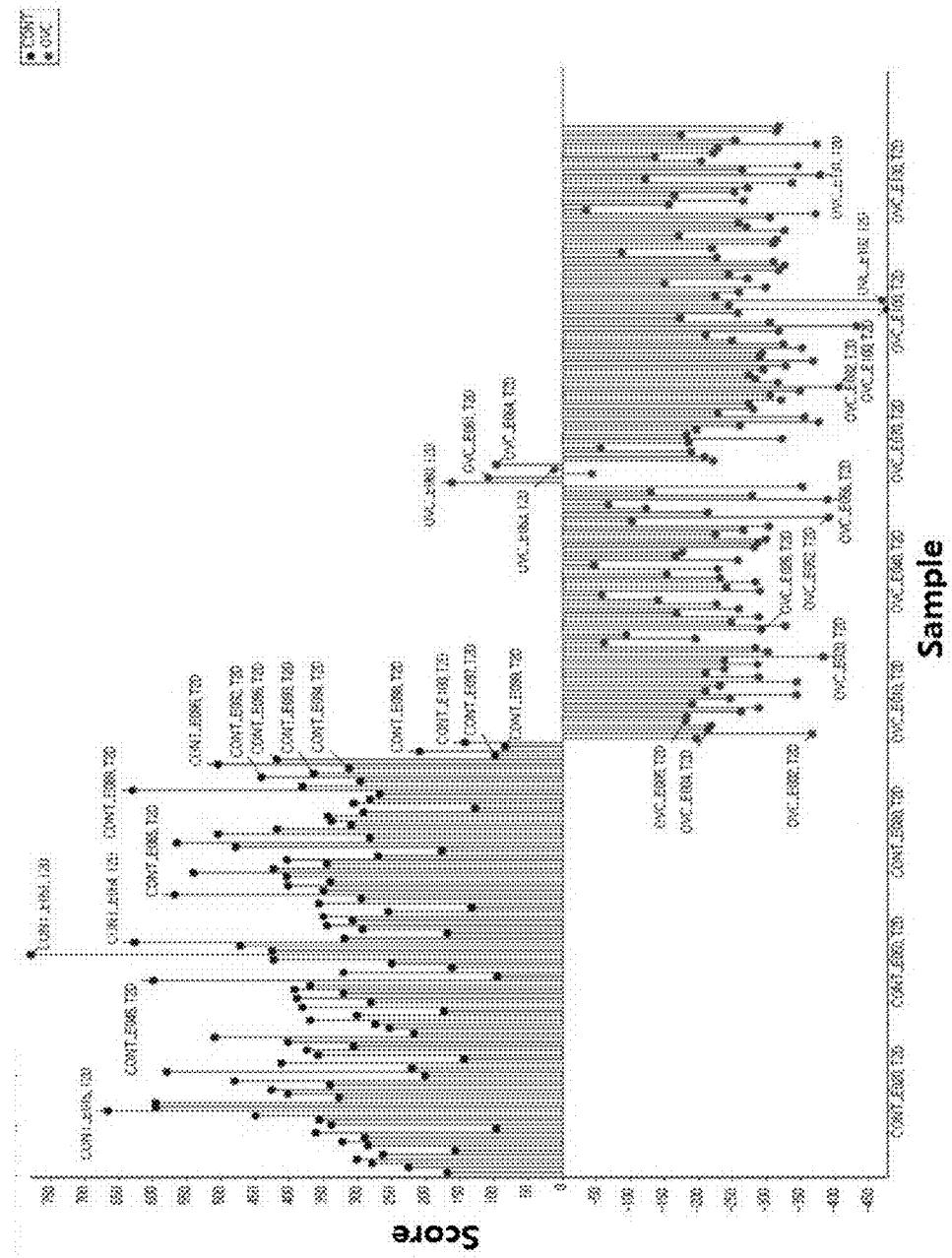
Figure 3B:
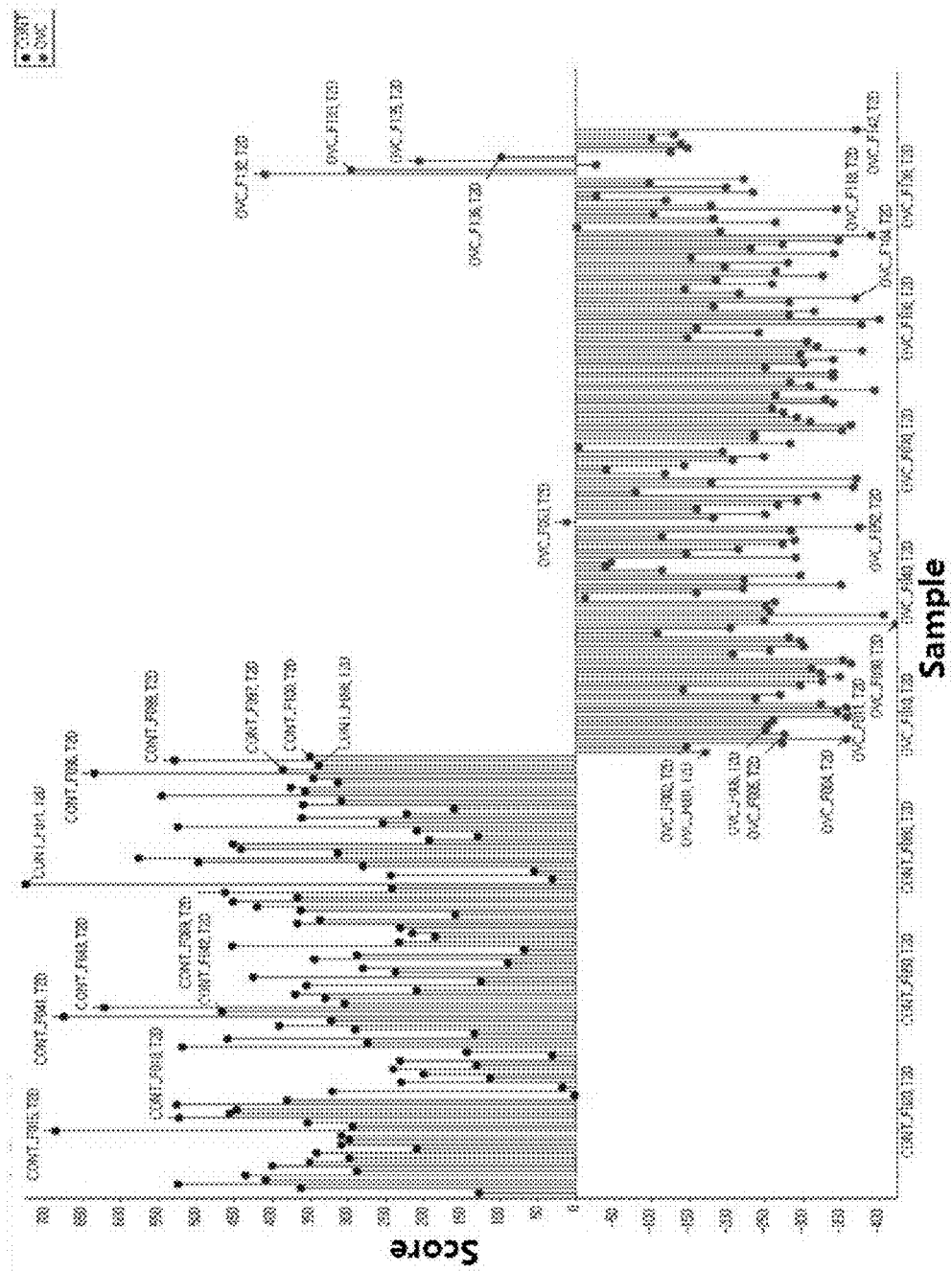

FIGS. 1 to 3 show discriminant scores obtained from ovarian cancer patients and non-ovarian cancer patients by PCA-DA. The experiment was repeated a total of six times, and thus each graph in FIGS. 1 to 3 shows the results of each experiment, and each of FIGS. 1 to 3 shows two graphs. In the results of the PCA-DA, the discriminant scores for the ovarian cancer scores are indicated by negative numbers (red dots on the graphs), and the discriminant scores for the non-ovarian cancer scores are indicated by positive numbers (blue dots on the graphs).

Figure 4A:
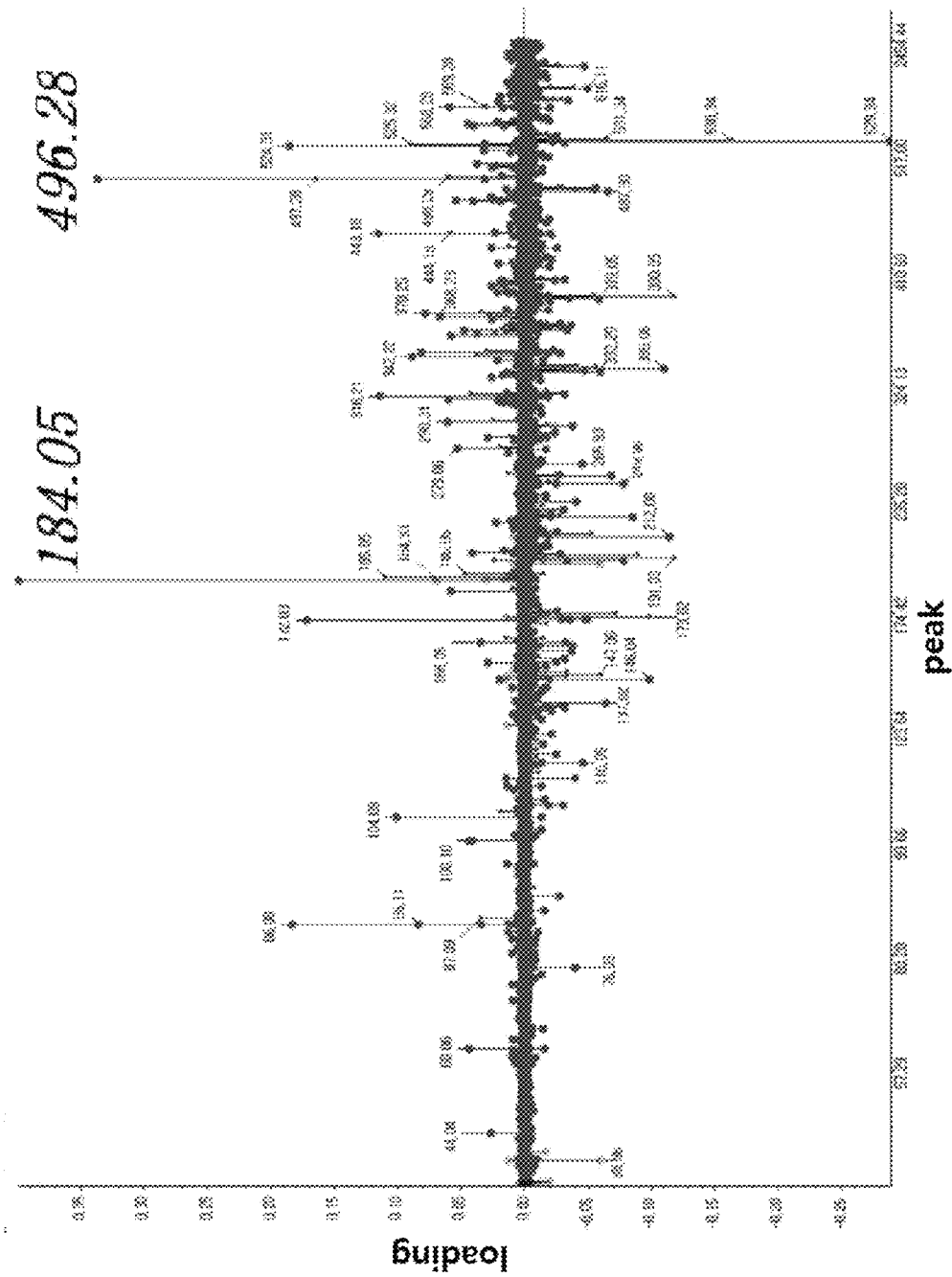
FIGS. 4a to 6b show low-mass ion peaks obtained from ovarian cancer patients (negative numbers) and non-ovarian cancer patients (positive numbers) by importing the mass spectra of low-mass ions, extracted using a MALDI-TOF mass spectrometer, into MarkerView™, followed by PCA-DA. The experiment was repeated six times in total, and thus each graph in FIGS. 4a to 6b shows the results of each experiment, and each of FIGS. 4a to 6b shows two graphs (4a and 4b, 5a and 5b, 6a and 6b).
Figure 4B:
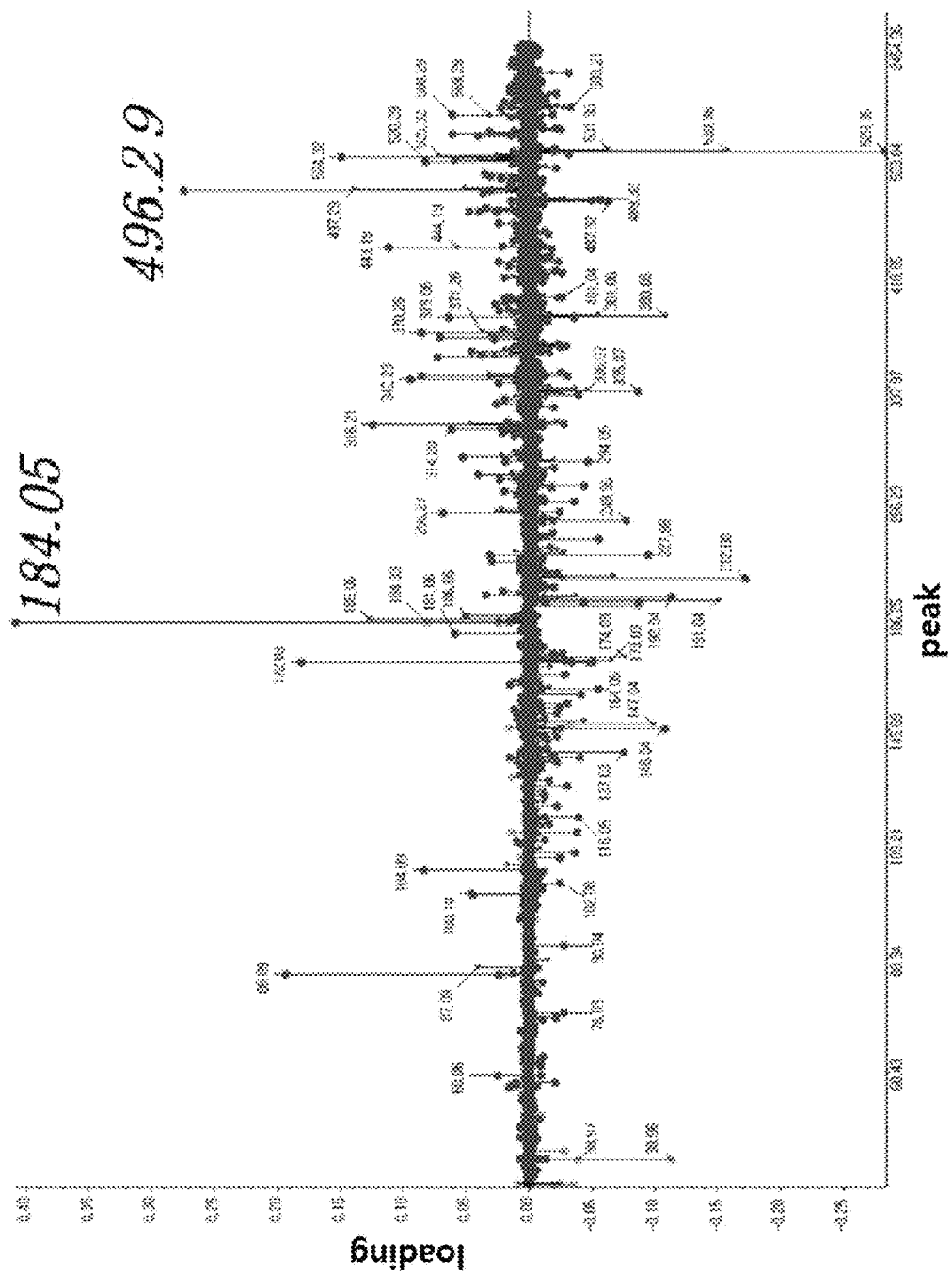
Figure 5A:
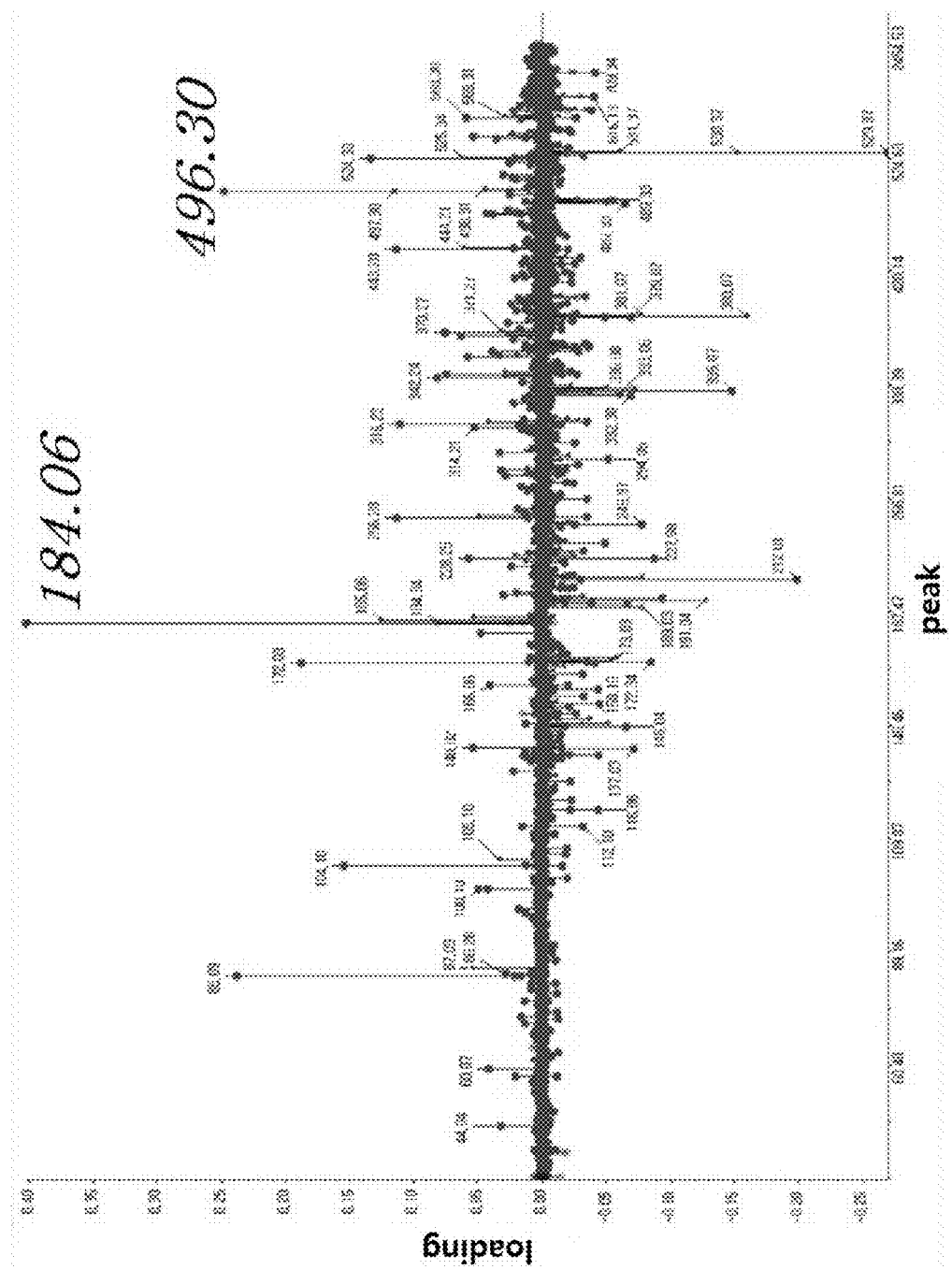
Figure 5B:
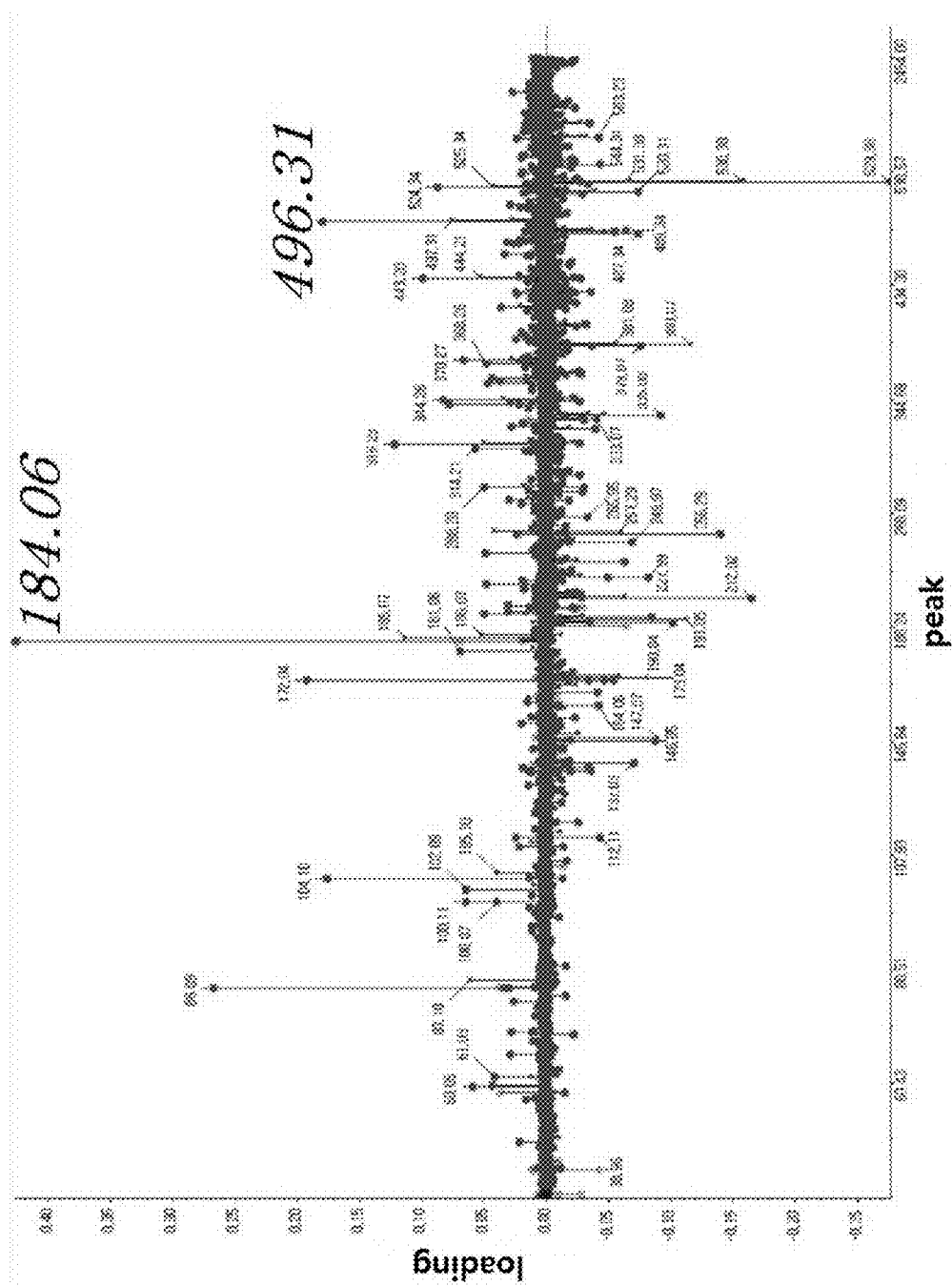
Figure 6A:
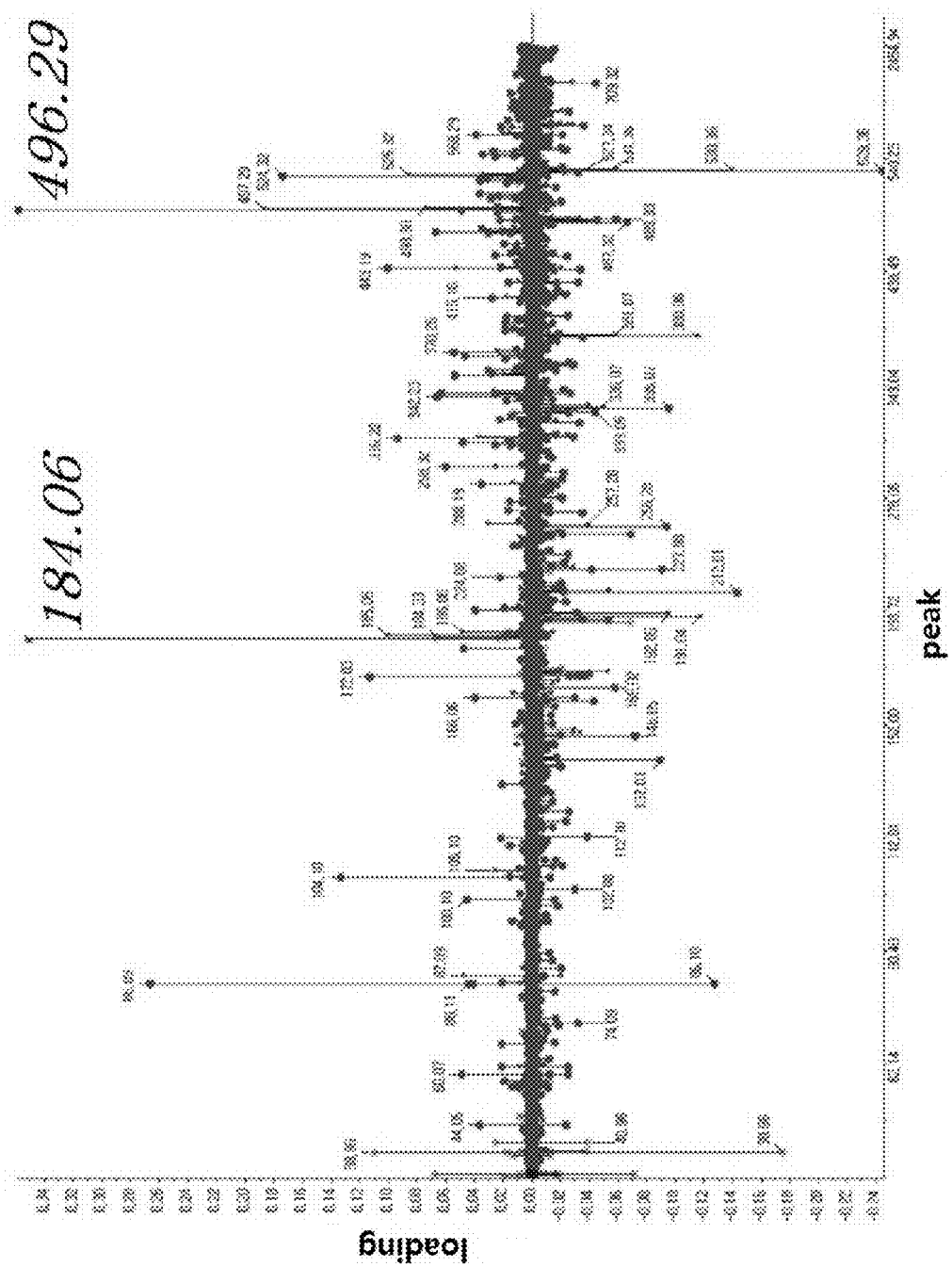
Figure 6B:
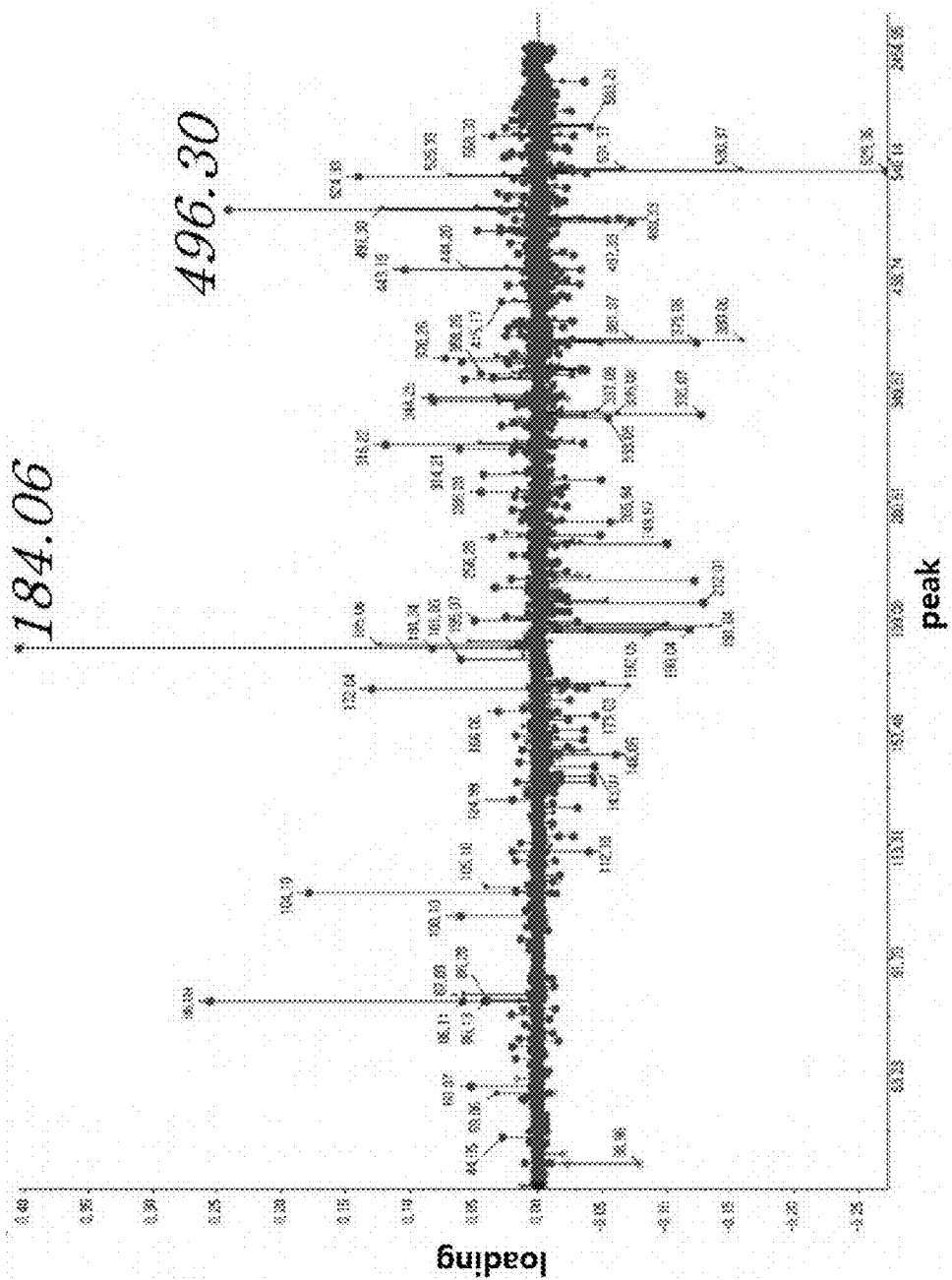

FIGS. 4 to 6 show low-mass ion peaks obtained from ovarian cancer patients (negative numbers) and non-ovarian cancer patients (positive numbers) by PCA-DA. The experiment was repeated a total of six times, and thus each graph in FIGS. 1 to 3 shows the results of each experiment, and each of FIGS. 1 to 3 shows two graphs. In the results of the six experiments, it was seen that a peak of 184 m/z and a peak of 496 m/z consistently showed a significant difference between the ovarian cancer patients and the non-ovarian cancer patients. Thus, these peaks were selected as low-mass ion peaks for diagnosis of ovarian cancer.

Example 2: Identification of Low-Mass Ions Corresponding to Low-Mass Ion Peaks for Diagnosis of Ovarian Cancer In order to identify substances showing the 184 m/z peak and 496 m/z peak selected in Example 1, the following experiment was performed.

2-1: Identification of Substance Showing Peak of 184 m/z

Substances showing a peak of 184 m/z were searched against the human metabolome database. Epinephrine and L-homocysteic acid were selected as the most promising candidates. Thus, the MS/MS patterns of epinephrine and L-homocysteic acid standard materials were analyzed in order to determine whether the 184 m/z peak was shown by L-homocysteic acid.

Figure 7A:
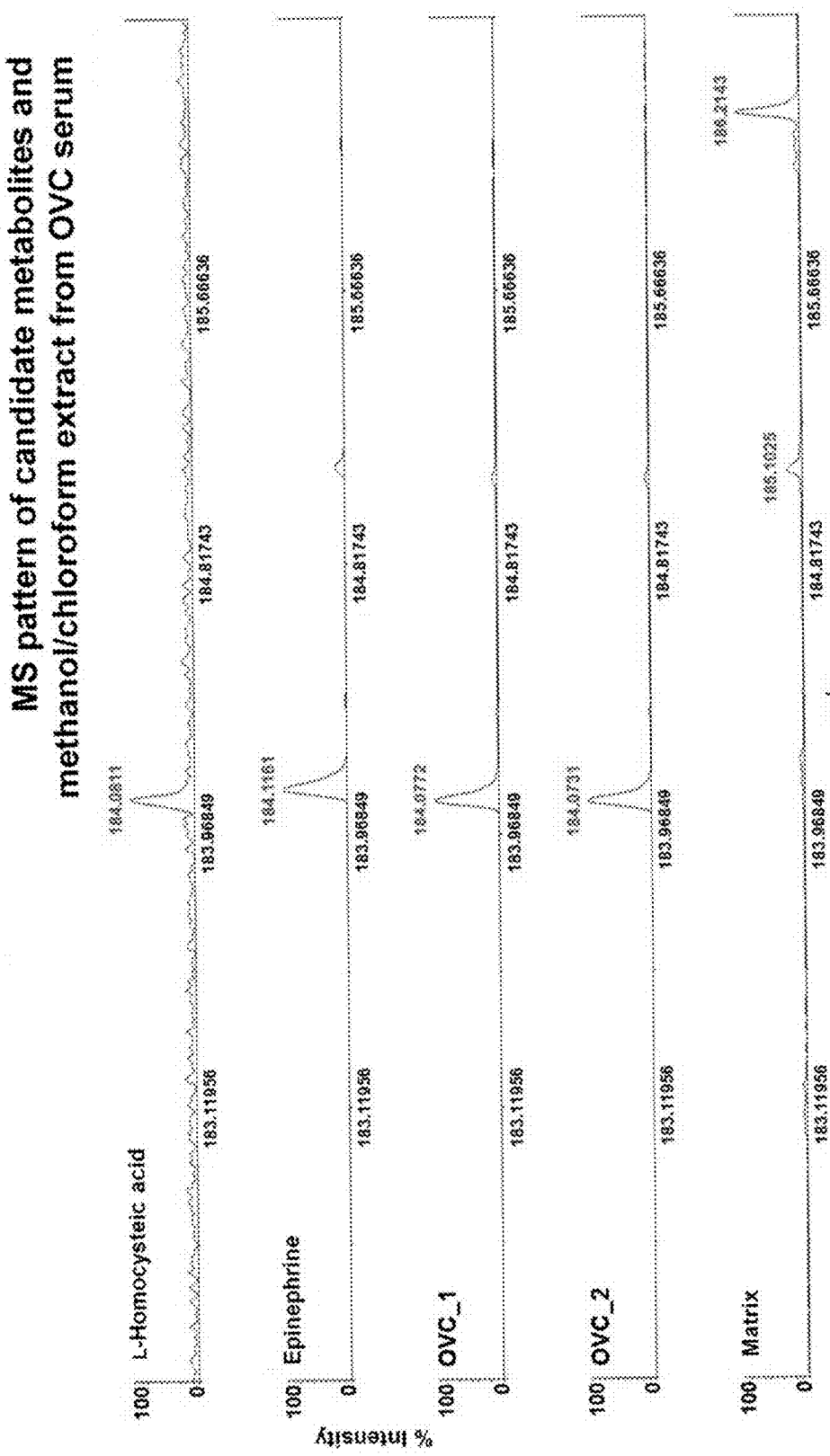
FIGS. 7a and 7b show that a low-mass ion for diagnosis of ovarian cancer, selected using MALDI-TOF, is L-homocysteic acid.
Figure 7B:
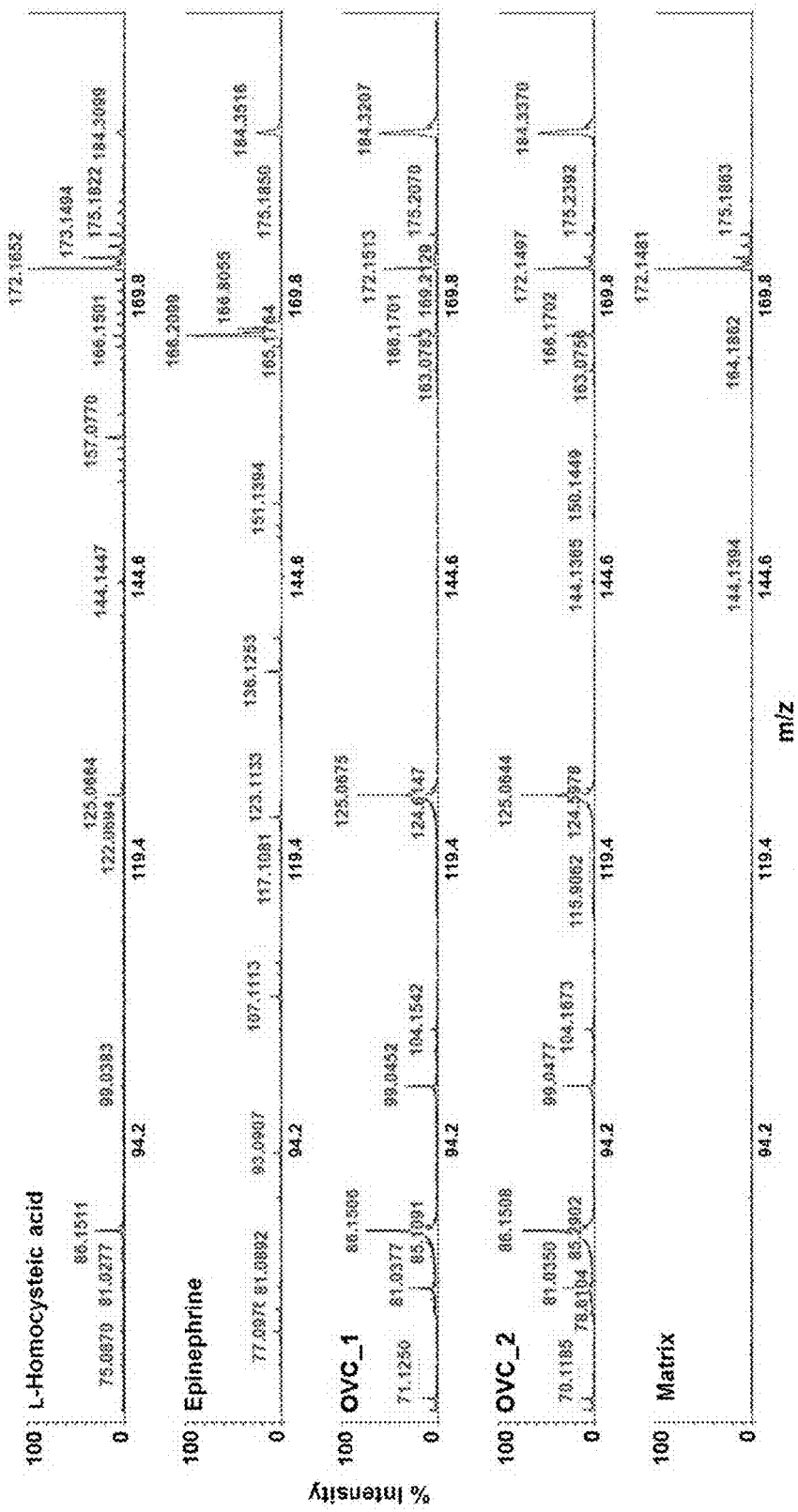

FIG. 7A shows the MS pattern of ovarian cancer patients, measured by the MALDI-TOF method, and FIG. 7B indicates that the MS/MS pattern of the 184 m/z peak shown in ovarian cancer patients is identical to the MS/MS pattern of L-homocysteic acid. Thus, it could be seen that the substance showing the 184 m/z peak was L-homocysteic acid.

2-2: Identification of Substance Showing Peak of 496 m/z

Figure 8A:
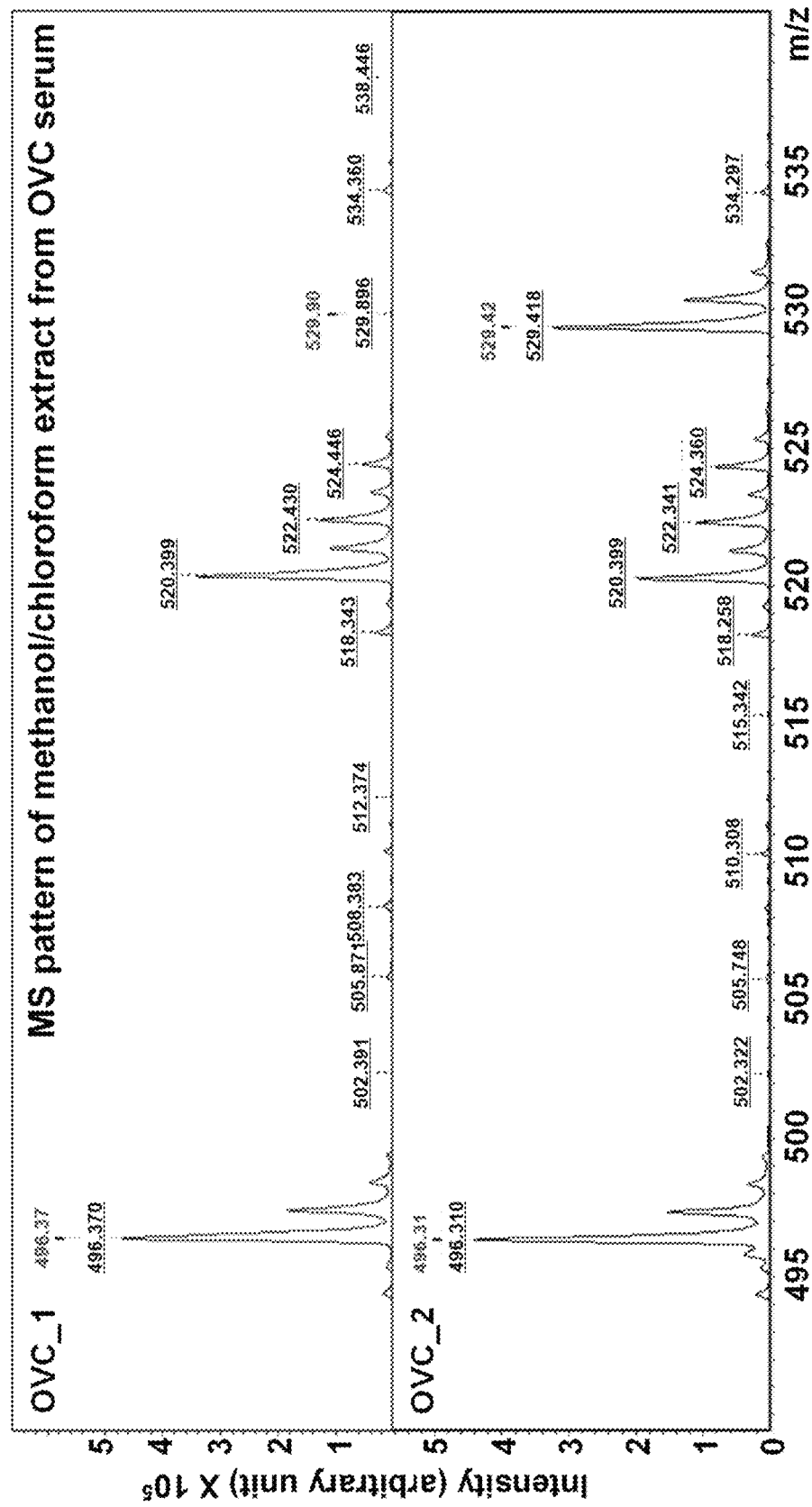
FIGS. 8a and 8b show that a low-mass ion for diagnosis of ovarian cancer, selected using MALDI-TOF, is lysophosphatidylcholine (16:0).
Figure 8B:
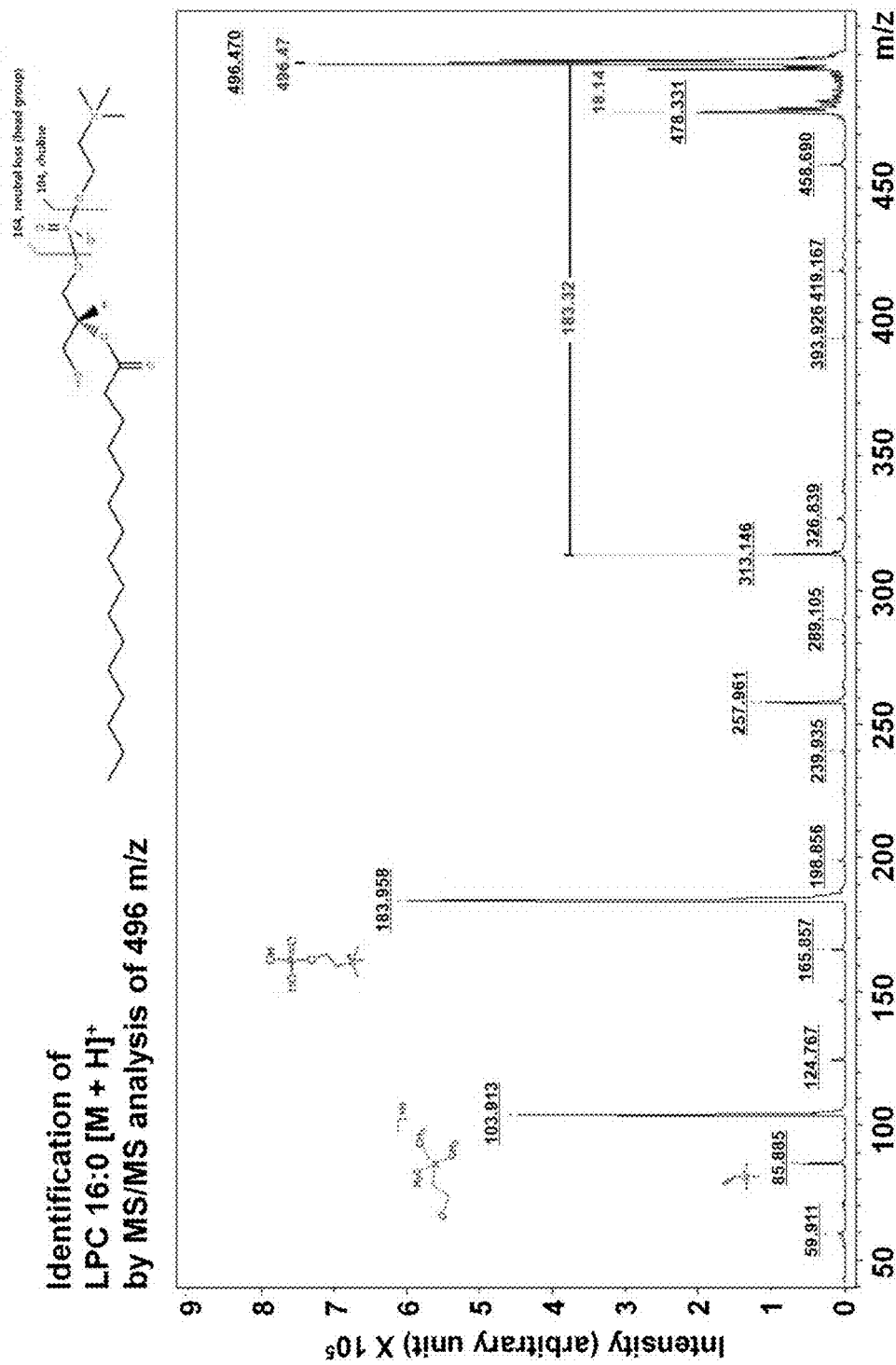

Substances showing a peak of 496 m/z were searched against the human metabolome database. A candidate showing this peak was found to be only lysophosphatidylcholine (16:0). FIG. 8A shows the MS pattern of ovarian cancer patients, measured by the MALDI-TOF method, and FIG. 8B indicates that the MS/MS pattern of the 496 m/z peak shown in ovarian cancer patients is identical to the MS/MS pattern of lysophosphatidylcholine (16:0). Thus, it could be seen that the substance showing the 496 m/z peak was lysophosphatidylcholine (16:0).

Example 3: Measurement of L-Homocysteic Acid

Figures 9A, 9B:
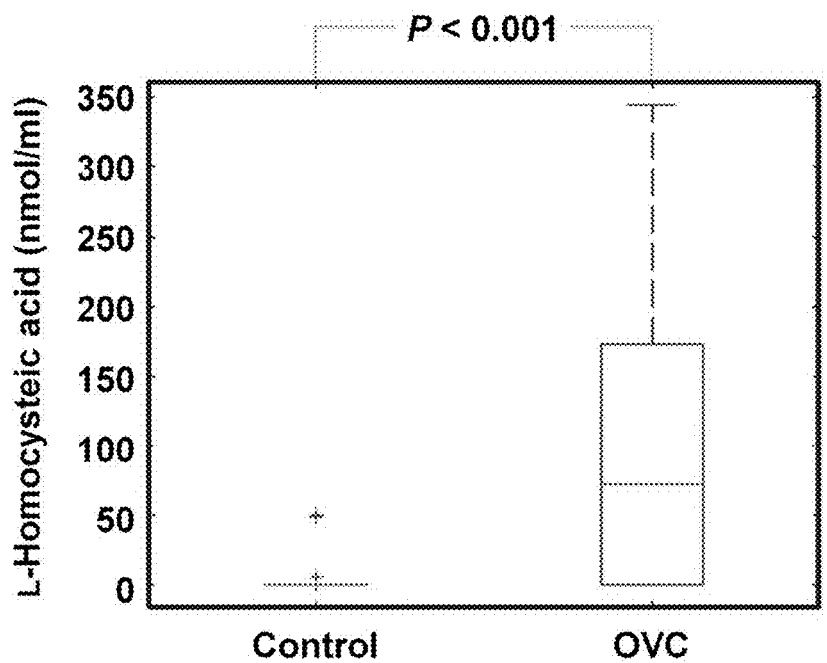
FIGS. 9a and 9b show that the concentration of L-homocysteic acid is higher in the sera of ovarian cancer patients than in the sera of non-ovarian cancer patients.

The concentration of L-homocysteic acid was measured using an L-homocysteic acid ELISA kit (Cusabio Biotech) according to the manufacturer's manual. Samples from 25 ovarian cancer patients were used, and samples from 64 non-ovarian cancer patients were used as a control. It was shown that the concentration of L-homocysteic acid was higher in the sera of the ovarian cancer patients than in the sera of the control (FIG. 9).

Example 4: Measurement of Lysophosphatidylcholine (16:0) in Blood

Because it was not easy to purchase lysophosphatidylcholine (16:0) standard material or ELISA kit, the concentrations of lysophosphatidylcholine (16:0) in ovarian cancer patients and non-ovarian cancer patients were relatively quantified by LC-MS/MS analysis. Samples from 25 ovarian cancer patients were used, and samples from non-ovarian cancer patients were used as a control.

The LC-MS/MS analysis was performed in the following manner.

A nanoflow HPLC instrument (Easy-nLC, Thermo Fisher Scientific) was coupled on-line to a LTQ mass spectrometer (Thermo Scientific). The analytical column (50 cm length and 75 um inner diameter) used was PepMap® RSLC (C18, 2 um, 100 Å). Reversed phase chromatography was performed with a binary buffer system consisting of 0.1% formic acid (buffer A) and acetonitrile in 0.1% formic acid (buffer B). The sample was separated with a linear gradient of 3-50% buffer B at a flow rate of 300 nL/min. The gradient time was 90 min, and the total run time for an LC MS/MS was 120 min. The extracted lysophosphatidylcholine (16:0) was analyzed by selected reaction monitoring (SRM) mode. The SRM transitions for lysophosphatidylcholine (16:0) lipid were set to m/z 496.4→183.96 and m/z 496.4→478.33. The SRM data were acquired within fragment ion mass±2 m/z, and each SRM transition and respective retention time were validated for specific LPC. Data were processed by integrating the appropriate peaks for lysophosphatidylcholine (16:0), followed by a comparison with the calculated peak area by two-paired t-test.

Figures 10A, 10B:
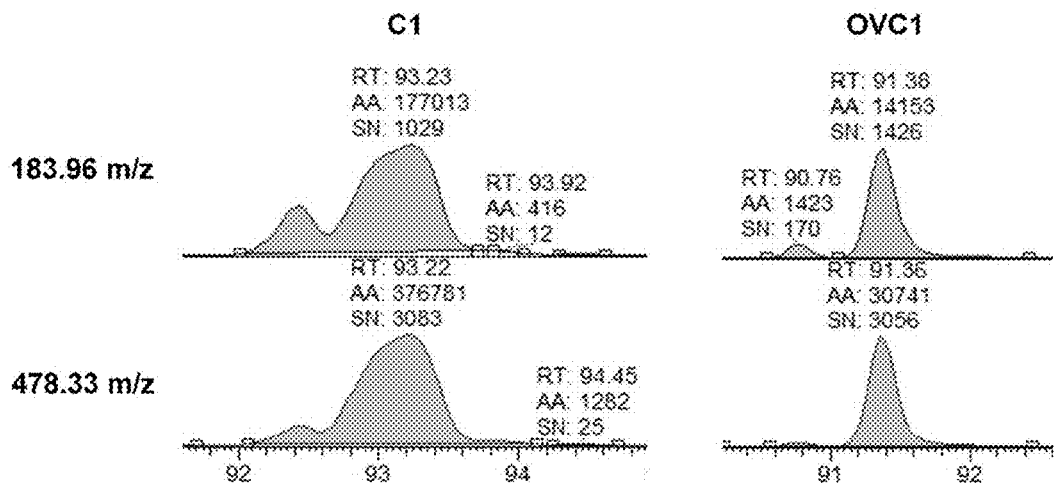
FIGS. 10a, 10b and 10c show that the concentration of lysophosphatidylcholine (16:0) is lower in the sera of ovarian cancer patients than in the sera of non-ovarian cancer patients.
Figure 10C:
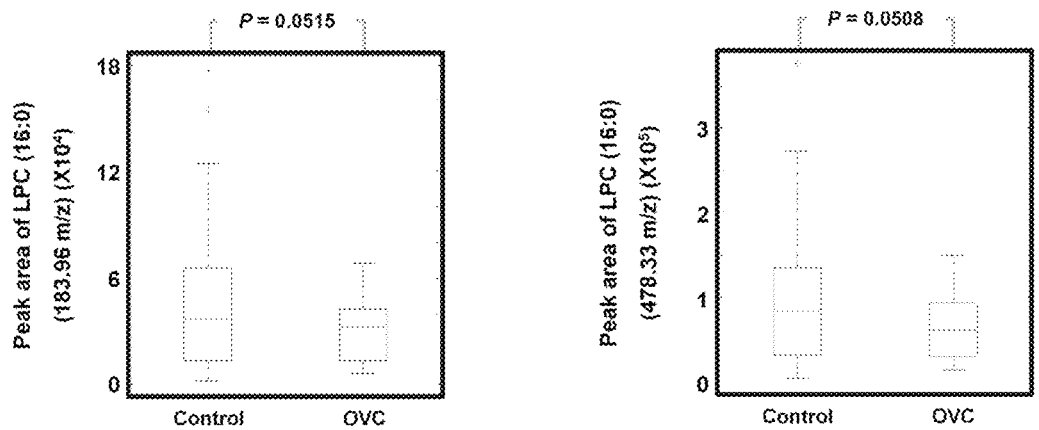

It was shown that the concentration of lysophosphatidylcholine (16:0) corresponding to the peak of 478.33 m/z and 183.96 m/z was lower in the sera of the ovarian cancer patients than in the sera of the non-ovarian cancer patients (FIG. 10).

Example 5: Construction of Diagnosis Method

As measures for determining the accuracy of diagnosis, sensitivity and specificity are used. "Positive" in the results of diagnosis means that the subject was affected by the disease of interest, and "negative" means that the subject was not attacked by the disease of interest. Under such definitions, sensitivity means the probability with which the result of diagnosis is "positive" when the subject was affected by the disease of interest, and specificity means the probability with which the result of diagnosis is negative when the subject was not affected by the disease of interest. In other words, as sensitivity and specificity are higher, the accuracy of diagnosis is higher.

The accuracy of ovarian cancer diagnosis based on the concentration of L-homocysteic acid measured in Example 3 was calculated. When a diagnosis method was constructed such that subjects having an L-homocysteic acid concentration higher than 10 nmol/ml, as detected by ELISA analysis, would be diagnosed as having ovarian cancer and subjects having an L-homocysteic acid concentration of 10 nmol/ml or lower would be diagnosed as having no ovarian cancer, sensitivity and specificity were calculated to be 64.0% and 100%, respectively.

The accuracy of ovarian cancer diagnosis based on the peak area of lysophosphatidylcholine (16:0) measured in Example 4 was calculated. When a diagnosis method was constructed such that subjects having a peak area of lysophosphatidylcholine (16:0) of less than 50,000 as determined by LC-MS/MS analysis would be diagnosed as having ovarian cancer and subjects having a peak area of lysophosphatidylcholine (16:0) of 50,000 or more would be diagnosed as having no ovarian cancer, sensitivity and specificity were calculated to be 76.0% and 47.4%, respectively.

From the above results, it was determined that the use of lysophosphatidylcholine (16:0) or L-homocysteic acid alone is insufficient for accurate diagnosis of ovarian cancer. Thus, the diagnosis method shown in FIG. 11 was constructed. According to this method, the concentrations of L-homocysteic acid in biological samples obtained from subjects were measured using a commercial ELISA kit. In biological samples obtained from non-ovarian cancer patients, no L-homocysteic acid was generally detected, and even if L-homocysteic acid was detected, the concentration of L-homocysteic acid detected ranged from 5 nmol/ml (that was significantly lower than that in ovarian cancer patients) to 10 nmol/ml. If the concentration of L-homocysteic acid detected is higher than 10 nmol/ml, the subject can be diagnosed as an ovarian cancer patient. If the concentration of L-homocysteic acid detected was 10 nmol/ml or lower, the concentration of lysophosphatidylcholine (16:0) in the biological sample obtained from the subject was measured using the LC-MS/MS method. If the concentration of lysophosphatidylcholine (16:0) in a biological sample obtained from a subject is lower than the concentration of lysophosphatidylcholine (16:0) in the biological sample from the non-ovarian cancer patient or is as low as the concentration of lysophosphatidylcholine (16:0) in the biological sample from the ovarian cancer patient, the subject can be diagnosed as an ovarian cancer patient. In the Example of the present invention, a subject showing a peak area of lysophosphatidylcholine (16:0) of less than 50,000 was diagnosed as an ovarian cancer patient, but the concentration of lysophosphatidylcholine (16:0) can vary depending on measurement conditions, measurement instruments and the amounts of samples. Thus, whether a subject is an ovarian cancer patient can be diagnosed by comparing the concentration of lysophosphatidylcholine (16:0) in a biological sample of the subject with the concentration of lysophosphatidylcholine (16:0) in a biological sample of a non-ovarian cancer patient as a negative control and/or a biological sample of an ovarian cancer patient as a positive control, obtained under the same conditions. Alternatively, standard numerical data obtained from non-ovarian cancer patients and ovarian cancer patients under standard conditions may also be used to diagnose whether a subject has ovarian cancer.

Figure 11:
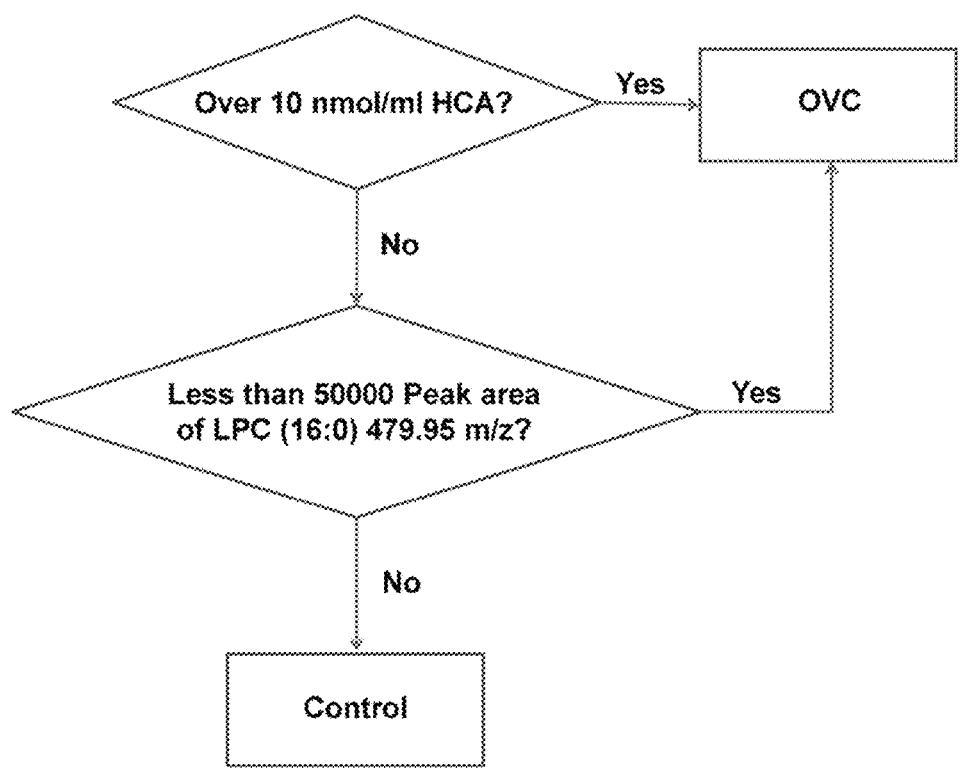
FIG. 11 schematically shows a method of diagnosing ovarian cancer based on the concentrations of L-homocysteic acid and lysophosphatidylcholine (16:0).

FIG. 11 is a schematic view showing a method of diagnosing ovarian cancer based on the concentrations of L-homocysteic acid and lysophosphatidylcholine (16:0).

When the diagnosis method of FIG. 11 was performed using samples obtained from 25 ovarian cancer patients and 19 non-ovarian cancer patients, sensitivity and specificity were calculated to be 88.0% and 73.68%, respectively.

As described above, the use of the present invention enables ovarian cancer to be diagnosed in a cost-effective, rapid and accurate manner. Thus, it is expected that the present invention can be effectively used to diagnose and treat ovarian cancer.

What is claimed is:

1. A kit for diagnosing ovarian cancer, which comprises:
   an antibody that binds specifically to lysophosphatidylcholine (16:0); and
   an antibody that binds specifically to L-homocysteic acid.

2. A method for treating a human subject, comprising:
   1) measuring the concentration of L-homocysteic acid in a serum or blood sample obtained from the subject;
   2) measuring the concentration of lysophosphatidylcholine (16:0) in a serum or blood sample obtained from the subject; and
   3) if the measured concentration of L-homocysteic acid is higher than that of a subject without ovarian cancer and/or the measured concentration of lysophosphatidylcholine (16:0) is lower than that of a subject without ovarian cancer, treating the subject for ovarian cancer.

3. The method of claim 2, wherein step 2) is performed after step 1).

4. The method of claim 2, wherein step 1) or step 2) comprises the steps of:
   A) acquiring the mass spectrum of the serum or blood sample obtained from the subject; and
   B) comparing the acquired mass spectrum with the mass spectrum of a serum or blood sample of a non-ovarian cancer patient or the mass spectrum of a serum or blood sample of an ovarian cancer patient to determine the difference in the concentration of lysophosphatidylcholine (16:0) or L-homocysteic acid therebetween.

5. The method of claim 2, wherein step 1) or step 2) is performed using an antigen-antibody binding reaction.

6. The method of claim 2, wherein step 1) is performed by measuring whether the concentration of L-homocysteic acid detected in the serum or blood sample collected from the subject is higher than 10 nmol/ml.

7. The method of claim 2, wherein step 1) is performed using ELISA (enzyme-linked immunosorbent assay), and step 2) is performed using LC-MS/MS.

* * * * *